United States Patent [19]

Smith

[11] 4,030,836

[45] June 21, 1977

[54] METHOD FOR MAPPING SURFACES WITH RESPECT TO ELLIPSOMETRIC PARAMETERS

[75] Inventor: Tennyson Smith, Thousand Oaks, Calif.

[73] Assignee: The United States of America as represented by the Secretary of the Air Force, Washington, D.C.

[22] Filed: Oct. 28, 1975

[21] Appl. No.: 626,148

[52] U.S. Cl. .............................................. 356/118
[51] Int. Cl.² ...................................... G01N 21/40
[58] Field of Search .......... 356/118, 119, 114, 209; 250/225

[56] References Cited

UNITED STATES PATENTS 2,731,878  1/1956  Sherwin ............................. 356/209

FOREIGN PATENTS OR APPLICATIONS 1,089,672  11/1967  United Kingdom ................ 356/201

OTHER PUBLICATIONS

Dignam, et al., "Azimuthal Misalignment & Surface Anisotropy As Sources of Error in Ellipsometry," Applied Optics, 8–1970, pp. 1868–1873.
McCartney, et al., "Determination of Proportions of Coal Components by Automated Microscopic Reflectance Scanning," Fuel vol. 50, 8-1971, pp. 226-235.

Primary Examiner—John K. Corbin
Assistant Examiner—Wm. H. Punter
Attorney, Agent, or Firm—Joseph E. Rusz; Willard R. Matthews, Jr.

[57] ABSTRACT

Ellipsometric parameters for a given structural member surface area are obtained by scanning the structural member surface area at an oblique angle with a polarized monochromatic light beam and receiving the reflected light beam with a rotating analyzer. The rotating analyzer outputs are detected at its 0°, 45° and 90° azimuth orientations by a photodetector. The photodetector outputs can be plotted in their proper relationship to the scanned surface area boundaries to provide maps useful in nondestructive testing and other applications. Equations are provided that permit the conversion of the photodetector outputs into ellipsometric physical parameter values for refractive index, absorption coefficient and material thickness. Scanning in one embodiment is accomplished by a structural member holding device that can be simultaneously rotated and vertically translated.

1 Claim, 4 Drawing Figures

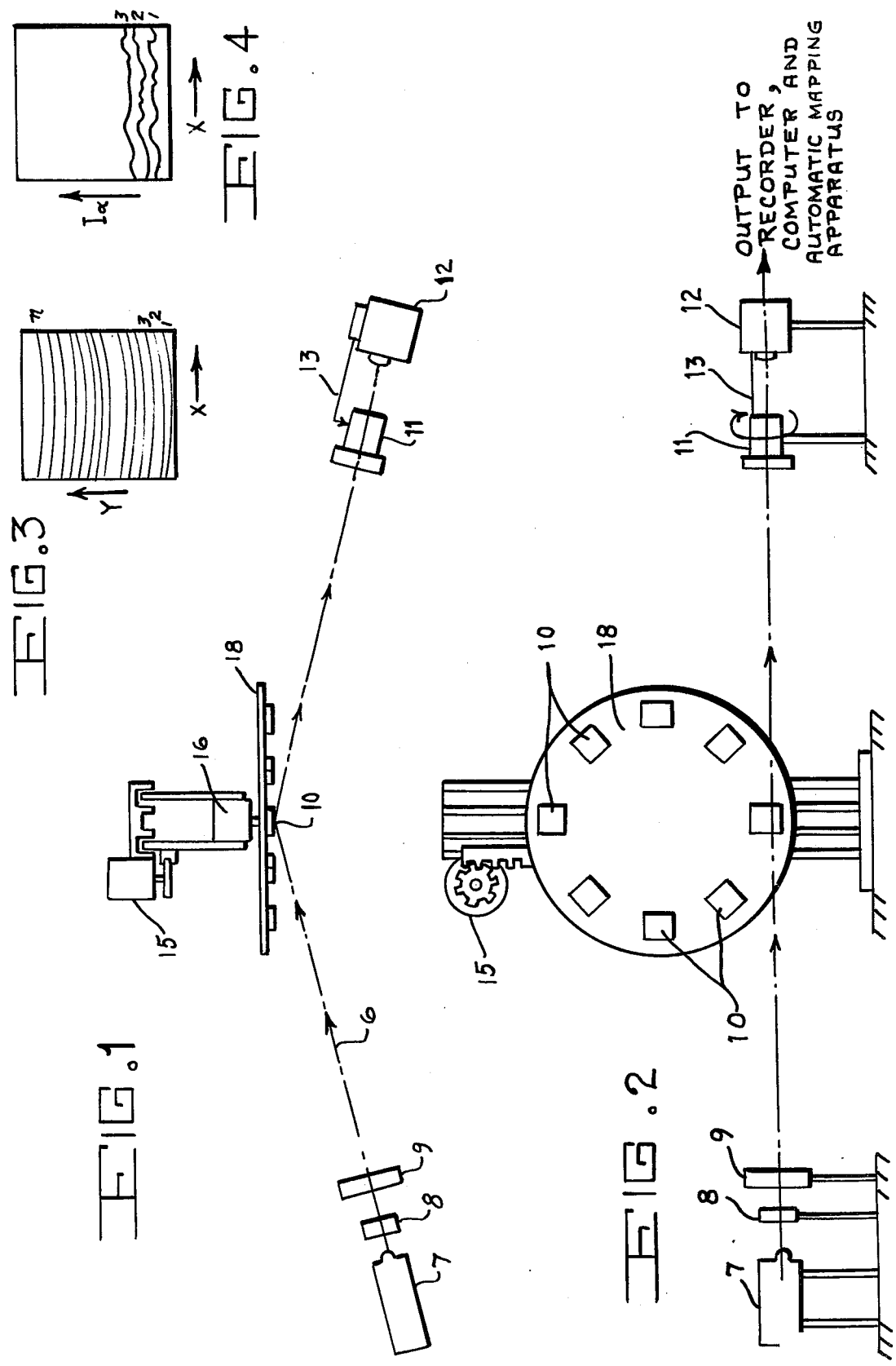

METHOD FOR MAPPING SURFACES WITH RESPECT TO ELLIPSOMETRIC PARAMETERS

STATEMENT OF GOVERNMENT INTEREST

The invention described herein may be manufactured and used by or for the Government for governmental purposes without the payment of any royalty thereon.

BACKGROUND OF THE INVENTION

This invention relates to the evaluation of structural surfaces, nondestructive testing and other utilizations of surface characteristics, and more particularly to the mapping of such surfaces with respect to ellipsometric parameters in order to predict failure areas for such applications as adhesion, corrosion, lubrication, and the like.

It is a conventional practice in preparing structural members for manufacture, surface finishing and final assembly to utilize certain maps to represent various surface characteristics. Such maps plot data, relating to corrosion, adhesion, lubrication and other characteristics and are known as application or surface maps (designated S-maps). In conjunction with these manufacturing procedures it would be desirable to provide further safeguards against failures in the final product. For example, after preparing a wing section for adhesive bonding it would be valuable to map the surface in order to predetermine areas that might fail and therefore need further treatment or need to be discarded.

The present invention is directed toward providing ellipsometric parameter maps (designated I-maps and P-maps) that define various surface and physical ellipsometric parameters that can be correlated with the S-maps. Such supplemental maps satisfy a current need by providing means for detecting many instances of potential failure as well as being a source of other manufacturing and safety information.

SUMMARY OF THE INVENTION

The invention comprehends mapping of structure surfaces with respect to ellipsometric parameters. Apparatus to accomplish this includes a source for producing a polarized monochromatic light beam, a rotating analyzer positioned to receive the light beam as it is reflected from the surface being mapped and a photodetector that receives the output of the analyzer. The photodetector output is triggered with the rotating analyzer in a manner that provides output signals for only 0°, 45° and 90° azimuth orientations of the rotating analyzer. The structure surface to be mapped is scanned by the light beam. This is accomplished by means of a holding device that accommodates a plurality of structure elements or samples. It comprises a rotating disc upon which the structure elements or samples are placed around the periphery. The disc is caused to rotate whereby the incident light beam sweeps across the structure elements. The disc is also motorized to translate either up or down so that the sweep across each structure element is translated a discrete increment and eventually the entire structure surface is uniformly scanned.

It is a principal object of the invention to provide new and improved method and means, utilizing ellipsometric techniques, for improving nondestructive testing, fabrication and structural component evaluation procedures.

It is another object of the invention to provide a method for mapping structural surfaces with respect to ellipsometric parameters.

It is another object of the invention to provide apparatus for providing ellipsometric parameter values for structural surfaces.

It is another object of the invention to provide new and improved means for scanning a structural member surface area with ellipsometric apparatus.

These, together with other objects, features and advantages of the invention, will become more readily apparent from the following detailed description when taken in conjunction with the illustrative embodiment in the accompanying drawings.

DESCRIPTION OF THE DRAWINGS

FIG. 1 is a plan view of one presently preferred embodiment of the invention;

FIG. 2 is an elevational view of the apparatus of FIG. 1;

FIG. 3 illustrates a structural member showing the tracer of light beam scan utilized in the practice of the invention; and FIG. 4 illustrates a partial ellipsometric parameter map corresponding to the scanned structural member of FIG. 3.

DETAILED DESCRIPTION OF THE PREFERRED EMBODIMENT

The invention comprehends the mapping of surfaces with respect to ellipsometric parameters in order to predict failure areas for such applications as adhesion, corrosion, lubrication, etc. Certain applications of the invention therefore require both laboratory equipment and procedures and field applications. After laboratory experiments have demonstrated correlations between the ellipsometric maps produced in accordance with the invention and conventional surface maps a portable scanning device is used for large parts in the field.

In order to map laboratory samples of the order of a few inches in dimension or less, the samples are placed on a rotating disc which in turn is automatically translated such that as the disc rotates an ellipsometric light beam (held in a fixed position) sweeps across the sample. Upon each revolution the sweep across the sample is translated a definite increment so that eventually the whole sample has been scanned. Apparatus of this type is hereinafter described in detail with reference to FIG. 1 of the drawings.

In the field operation where surfaces of structural parts, wing panels, etc., are too large to place in the laboratory instrument, the ellipsometric components are placed in a scanning head. The scanning head is passed over the part in a systematic way, yielding a complete map of the surface.

FIGS. 1 and 2 show schematic representations of the laboratory embodiment. In the plan view of FIG. 1, the light beams from the light source 7 passes through monochromator 8 and polarizer 9 and reflects from the surface of sample 10. Upon reflection from sample 10 the light becomes elliptically polarized and passes through rotating analyzer 11. The rotating analyzer has an electronic trigger arrangement 13 such that the signal from the photodetector 11 is monitored and stored at precisely 0°, 45° and 90° azimuth. The signals are designated $I_0$, $I_{45}$ and $I_{90}$ since I is directly proportional to the light intensity. The relationships between the ellipsometric parameters $\Delta$, $\psi$, R, and I are $$\psi = \left(\frac{1}{2}\right) \arccos\left\{1 - \frac{2 I_0}{I_{90} + I_0}\right\} \quad (1)$$

$$\Delta = \arccos\left\{\frac{\left(\frac{2 I_{45}}{I_0 + I_{90}}\right) - 1}{\sin 2\chi}\right\} \quad (2)$$

where $$R = I_r/I_i \quad (3)$$

$$\Delta = f(n,k,d) \quad (4)$$

$$\psi = f(n,k,d) \quad (5)$$

$$R = f(n,k,d) \quad (6)$$

The relationship between $\Delta$, $\psi$, and R and the refractive index $n$, absorption coefficient $k$ and film thickness $d$ are exact but complex. The physical parameters $n$, $k$, and $d$ are usually computed from the ellipsometric parameters $\Delta$, $\psi$, and R. The invention comprehends both the idea of mapping and the experimental arrangement for mapping the sample surfaces with respect to ellipsometric parameters. The side view of FIG. 2 illustrates this. As the rotor disc sample holder 18 rotates by means of motor 16 the light beam 6 sweeps in an arc across the samples 10. As the sample sweeps through one pass the rotating analyzer 11 takes data $I_0$, $I_{45}$, and $I_{90}$ at a rate which depends upon the velocity of the analyzer. If analyzer 11 rotates rapidly with respect to the rotation speed of the disc-sample-holder 18 essentially continuous maps are recorded. The map diagram of FIG. 4 illustrates a typical map of the scanned sample of FIG. 3. The translator motor 15 moves the disc-sample-holder 18 up or down at a constant velocity such that each revolution of the disc yields a new sweep across the sample, e.g., sweeps 1, 2 and 3, etc. of FIG. 3.

The relationship between the values of I and the corresponding position on the sample is determined from the map. Between samples the light beam is reflected away from the analyzer which has a yield I = 0 until a new sample is reached. This locates the sample edges and allows the precise $x$ position to be determined. Similarly the $y$ coordinates are determined by the sweep I = 0 as the light misses the top and bottom of the sample. The recorder zero is automatically adjusted by a known increment upon each revolution so that the map traces are shifted with respect to each other.

Maps of $I_0$, $I_{45}$ and $I_{90}$ may be found to have relationships with corrosion, adhesion, or other types of surface maps (designated S-maps). In this case it would not be necessary to process the I-maps further in order to use them for practical purposes, such as predicting failure areas. However, the I-maps may not correlate with S-maps, whereas maps of the physical parameters, $n$, $k$, $d$ might. In this case it would be necessary to process the I-maps with Equations 1 through 6 to produce physical maps (P-maps). This can be automated by recording the I data on tape which then can be used to compute and map $n$, $k$, $d$ directly with a computer.

Mapping with respect to other surface parameters in place or in addition to ellipsometry falls within the scope of this invention. For example, other measurements such as surface potential, exo-electron current, or chemical composition by Auger spectroscopy can be obtained using the method of the invention. However, mapping with respect to Auger spectroscopy must be done with the surface under vacuum. This would not complicate the laboratory embodiment too much but would necessitate a suction cup type arrangement for field mapping applications.

While the invention has been described in its preferred embodiment, it is understood that the words which have been used are words of description rather than words of limitation and that changes may be made within the purview of the appended claims without departing from the scope and spirit of the invention in its broader aspects.

What is claimed is:

1. The method of mapping and utilizing for nondestructive testing purposes certain ellipsometric parameters of a discrete surface area of a structural member comprising the steps of scanning said discrete surface area from an oblique angle with a polarized monochromatic light beam, analyzing the light beam reflected from said surface area with a rotating analyzer, detecting with detector means the outputs of the rotating analyzer, recording the output values of the detector means for rotating analyzer azimuth orientation of 0°, 45° and 90° at a multiplicity of positions along each sweep of light beam scan, deriving ellipsometric parameters from said recorded output values by means of equations $$\psi = (\tfrac{1}{2} \arccos\left\{1 - \frac{2 I_0}{I_{90} + I_0}\right\},$$

$$\Delta = \arccos\left\{\frac{\left(\frac{2 I_{45}}{I_0 + I_{90}}\right)^{-1}}{\sin 2\psi}\right\}, \text{ and}$$

$$R = I_r/I_i,$$

plotting, for each rotating analyzer azimuth orientation, the ellipsometric parameter values at their appropriate coordinate positions relative to the scanned surface area boundaries, converting the derived ellipsometric parameter values into values of ellipsometric physical parameters for refractive index, absorption coefficient and material thickness, plotting said ellipsometric physical parameter values at their appropriate coordinate positions relative to the scanned surface area boundaries, and correlating said plotted ellipsometric parameter values and said plotted ellipsometric physical parameter values with an S-map of said discrete surface area.

* * * * *